(12) United States Patent
Hattori et al.

(10) Patent No.: US 12,724,011 B2
(45) Date of Patent: Sep. 1, 2026

(54) METHOD FOR ANALYZING AMINO ACIDS AND/OR ACYLCARNITINES

(71) Applicants: SHIMADZU CORPORATION, Kyoto (JP); NATIONAL UNIVERSITY CORPORATION SHIMANE UNIVERSITY, Shimane (JP)

(72) Inventors: Takanari Hattori, Kyoto (JP); Jun Watanabe, Kyoto (JP); Kengo Maeda, Kyoto (JP); Hironori Kobayashi, Izumo (JP); Yoshitomo Notsu, Izumo (JP)

(73) Assignees: SHIMADZU CORPORATION, Kyoto (JP); NATIONAL UNIVERSITY CORPORATION SHIMANE UNIVERSITY, Shimane (JP)

( * ) Notice: Subject to any disclaimer, the term of this patent is extended or adjusted under 35 U.S.C. 154(b) by 287 days.

(21) Appl. No.: 18/753,534

(22) Filed: Jun. 25, 2024

(65) Prior Publication Data

US 2025/0003930 A1 Jan. 2, 2025

(30) Foreign Application Priority Data

Jun. 29, 2023 (JP) ................................ 2023-107061

(51) Int. Cl.
*G01N 30/72* (2006.01)
*G01N 33/68* (2006.01)

(52) U.S. Cl.
CPC ..... *G01N 30/7233* (2013.01); *G01N 33/6812* (2013.01); *G01N 33/6848* (2013.01)

(58) Field of Classification Search
CPC ........... G01N 30/7233; G01N 33/6812; G01N 33/6848
See application file for complete search history.

(56) References Cited

U.S. PATENT DOCUMENTS

2014/0194304 A1* 7/2014 Shi ..................... G01N 33/6848 435/7.92
2021/0296105 A1* 9/2021 Ukai ..................... H01J 49/005

FOREIGN PATENT DOCUMENTS

EP 3605077 B1 * 4/2023 .......... H01J 49/0031

OTHER PUBLICATIONS

Shigematsu, Mass spectrometry by Newborns Mass Screening Reality; The Realities of Newborn Screening by Tandem Mass Spectrometry in Japan, Journal of the Mass Spectrometry Society of Japan, 2016, pp. 127-131, vol. 64, No. 4.

(Continued)

*Primary Examiner* — Nicole M Ippolito
(74) *Attorney, Agent, or Firm* — Paratus Law Group, PLLC

(57) ABSTRACT

First and second MRM transitions for a target substance, a first reference value concerning a measured intensity of the first MRM transition, and a second reference value concerning the measured-intensity ratio between the first and second MRM transitions are set. MRM measurements of an analyte sample using the first and second MRM transitions are performed to obtain a first intensity of the first MRM transition and a second intensity of the second MRM transition (Steps 11 and 12). The value of the first intensity is compared with the first reference value to determine whether the target substance is possibly contained (first determination; Step 14). For a target substance considered to be possibly contained in the analyte sample, the ratio between the first and second intensities is compared with the second reference value to determine whether the target substance is contained (second determination; Step 18).

7 Claims, 11 Drawing Sheets

(56) References Cited

OTHER PUBLICATIONS

Ishikawa et al., In tandem mass testing by waxing; Effects on leucine and isoleucine determination, Japanese Journal of Neonatal Screening, 2020, pp. 31(257)-43(269), vol. 30(3).
Saito et al., Essential oils for newborns—Three cases of false positive diagnosis of medium-chain acyl-CoA dehydrogenase deficiency in serum ELISA; Essential oils can cause false positive results of MCAD deficiency in newborn screening, Japanese Journal of Neonatal Screening, 2020, p. 102(196), vol. 30(2).
Nomachi et al., Pilot study of neonatal mass screening using a tandem mass spectrometer, 2008 year (four year) Implementation Results, Sapporo City Institute of Public Health Annual Report, 2009, pp. 42-48, vol. 36.

* cited by examiner

Fig. 2

| Compound Name | Target Disease | CE | Target MRM | Ref. Value | 1st Analysis Qualifier MRM | Intensity Ratio | 2nd Analysis Qualifier MRM | Thresh-old |
|---|---|---|---|---|---|---|---|---|
| Compound A | Disease 1 | CE_a | PreAt > ProAt | Tta | PreAq1 > ProAq1 | Ra | PreAq2 > ProAq2 | Tqa |
| Compound B | Disease 2 | CE_b | PreBt > ProBt | Ttb | PreBq1 > ProBq1 | Rb | PreBq2 > ProBq2 | Tqb |
| Compound C | Disease 3 | CE_c | PreCt > ProCt | Ttc | PreCq1 > ProCq1 | Rc | PreCq2 > ProCq2 | Tqc |
| Compound D | Disease 4 | CE_d | PreDt > ProDt | Ttd | PreDq1 > ProDq1 | Rd | PreDq2 > ProDq2 | Tqd |
| Compound E | Disease 5 | CE_e | PreEt > ProEt | Tte | PreEq1 > ProEq1 | Re | PreEq2 > ProEq2 | Tqe |
| ... | ... | ... | ... | ... | ... | ... | ... | ... |

Fig. 3

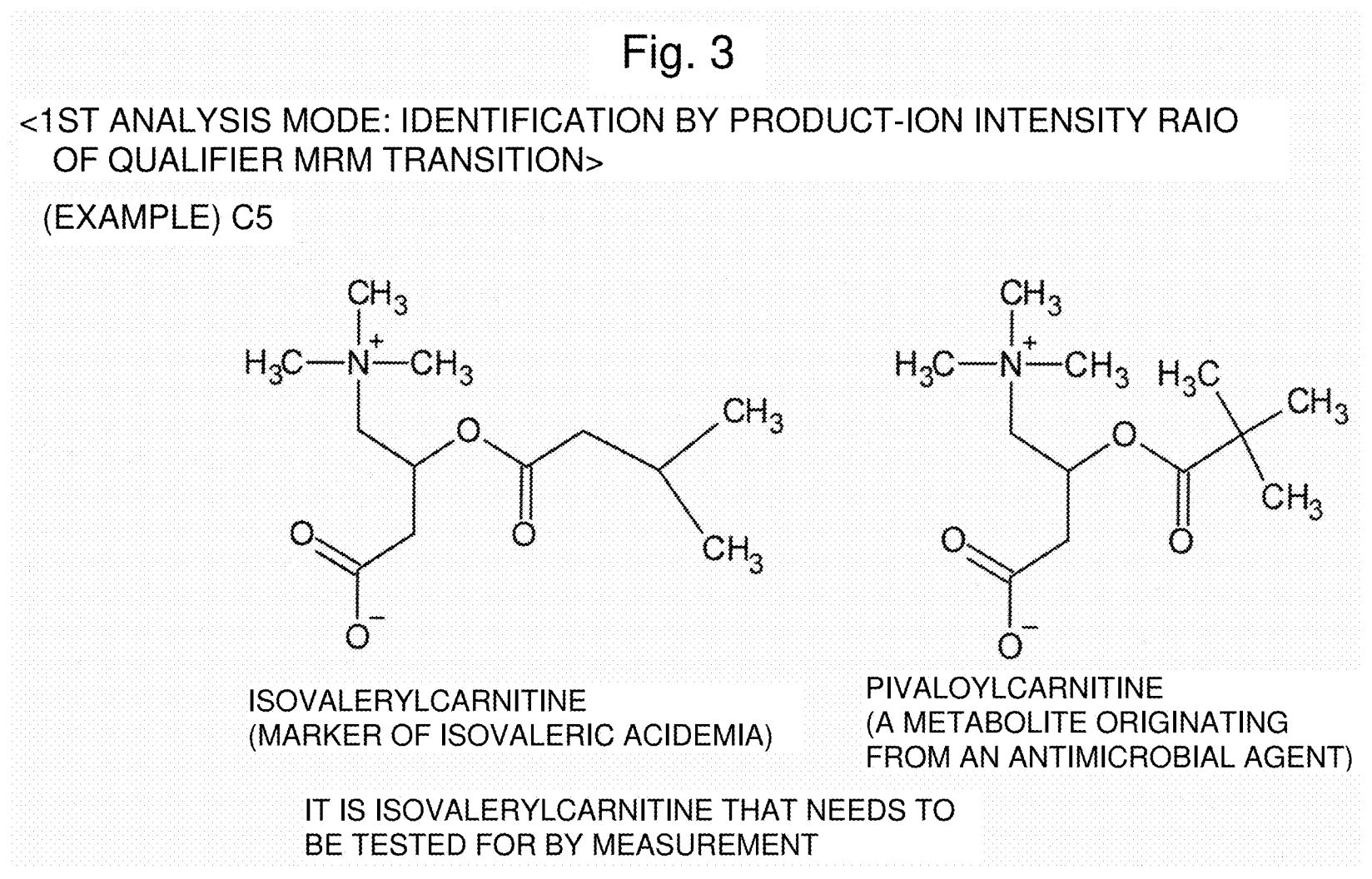

<1ST ANALYSIS MODE: IDENTIFICATION BY PRODUCT-ION INTENSITY RAIO OF QUALIFIER MRM TRANSITION>

(EXAMPLE) C5

ISOVALERYLCARNITINE
(MARKER OF ISOVALERIC ACIDEMIA)

PIVALOYLCARNITINE
(A METABOLITE ORIGINATING FROM AN ANTIMICROBIAL AGENT)

IT IS ISOVALERYLCARNITINE THAT NEEDS TO BE TESTED FOR BY MEASUREMENT

Fig. 5

FOR EXAMPLE, DEGREE OF SIMILARITY OF QUALIFIER-ION RATIO IS CONVERTED INTO SCORE TO BE USED FOR IDENTIFICATION AS FOLLOWS

WITH MAXIMUM SIMILARITY DEFINED AS 100, CALCULATE A SCORE OF DIFFERENCE IN QUALIFIER-ION RATIO BETWEEN STANDARD AND REAL SPECIMEN

■QUALIFIER-ION RATIO OF i-C5 FOR STANDARD: 20.44%

■QUALIFIER-ION RATIO FOR REAL SPECIMENS: SPECIMEN 1, 20.48%; SPECIMEN 2, 28.21%

SPECIMEN 1: i-C5 SCORE = 100 - (|20.48-20.44| / 20.44 x 100)
= 99.78

SPECIMEN 2: i-C5 SCORE = 100 - (|28.21-20.44| / 20.44 x 100)
= 61.99

SPECIMEN 1 IS CONSIDERED TO BE i-C5 SINCE IT HAS A HIGH SCORE

SPECIMEN 2 IS NOT CONSIDERED TO BE i-C5 SINCE IT HAS A LOW SCORE

Fig. 6

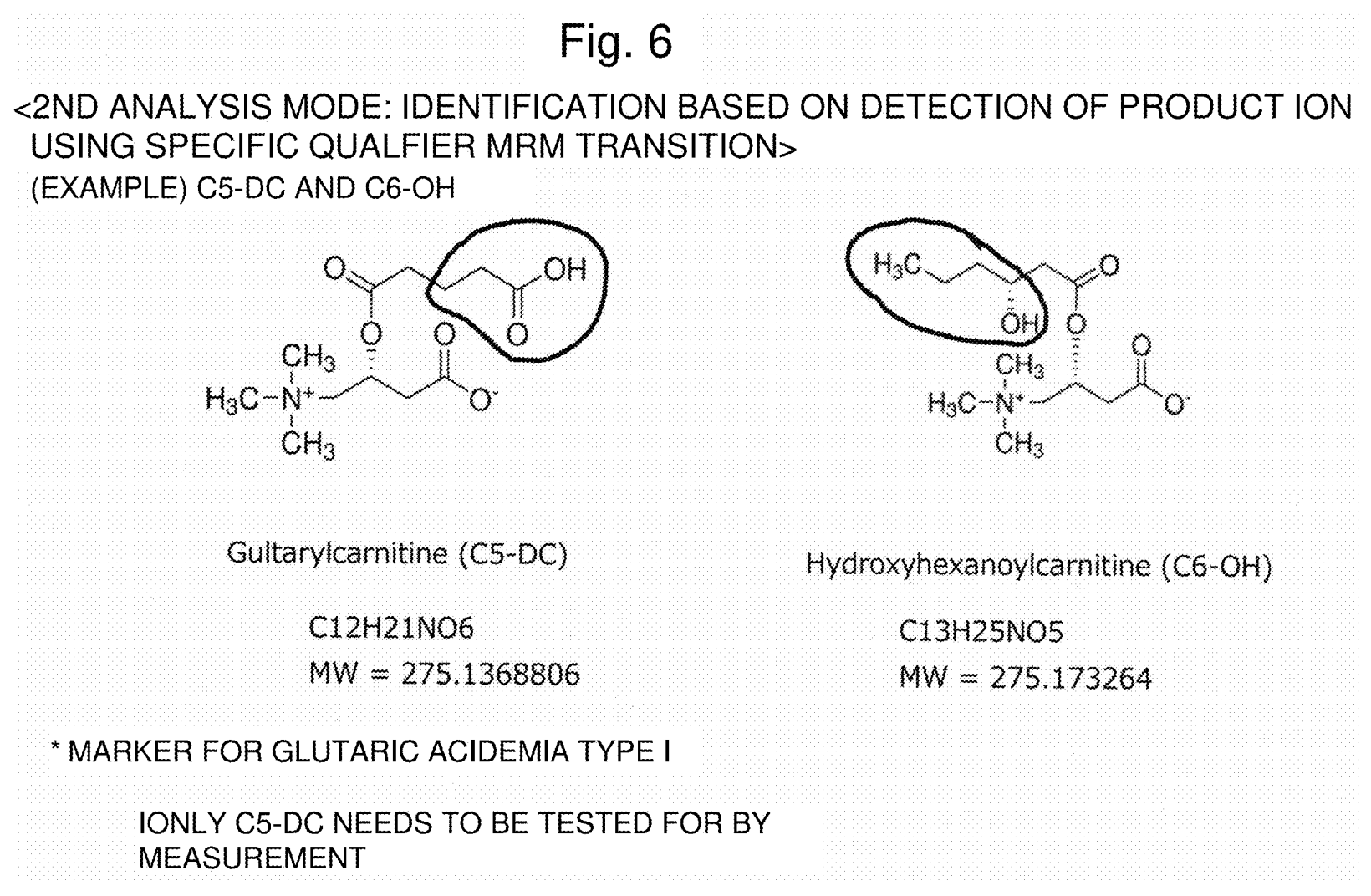

<2ND ANALYSIS MODE: IDENTIFICATION BASED ON DETECTION OF PRODUCT ION USING SPECIFIC QUALFIER MRM TRANSITION>

(EXAMPLE) C5-DC AND C6-OH

| Gultarylcarnitine (C5-DC) | Hydroxyhexanoylcarnitine (C6-OH) |
| --- | --- |
| C12H21NO6 | C13H25NO5 |
| MW = 275.1368806 | MW = 275.173264 |

* MARKER FOR GLUTARIC ACIDEMIA TYPE I

IONLY C5-DC NEEDS TO BE TESTED FOR BY MEASUREMENT

Fig. 7

PRODUCT ION SCAN (PRECURSOR ION: m/z 276.1, POSITIVE)

C5-DC

C6-OH

CE: -30 V m/z 276/87 IS DETECTED FROM C5-DC, BUT NOT FROM C6-OH

Fig. 8

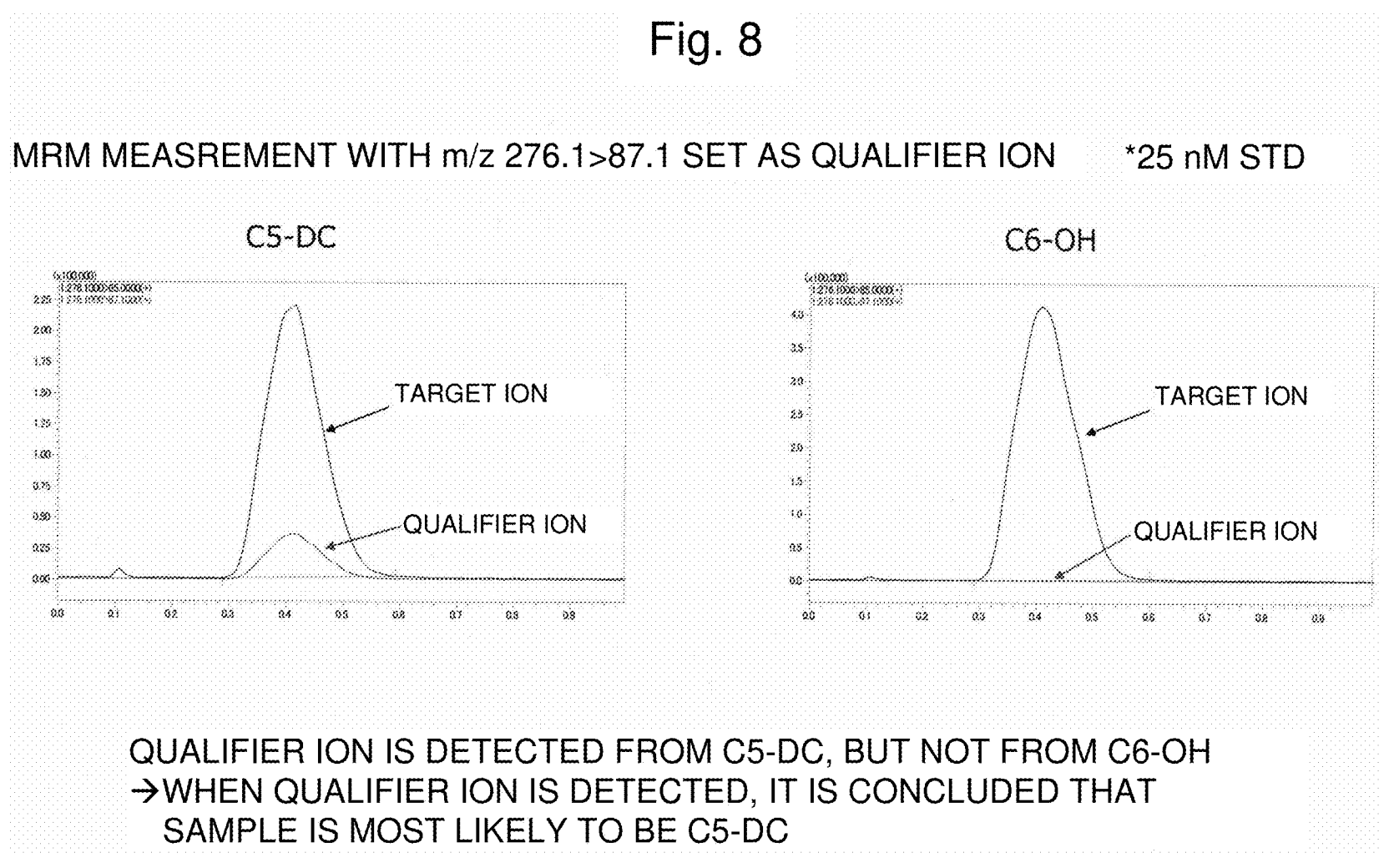

MRM MEASREMENT WITH m/z 276.1>87.1 SET AS QUALIFIER ION *25 nM STD

C5-DC

TARGET ION

QUALIFIER ION

C6-OH

TARGET ION

QUALIFIER ION

QUALIFIER ION IS DETECTED FROM C5-DC, BUT NOT FROM C6-OH

→WHEN QUALIFIER ION IS DETECTED, IT IS CONCLUDED THAT SAMPLE IS MOST LIKELY TO BE C5-DC

METHOD FOR ANALYZING AMINO ACIDS AND/OR ACYLCARNITINES

CROSS REFERENCE TO PRIOR APPLICATION

This application claims benefit to Japanese Patent Application No. 2023-107061 (filed on Jun. 29, 2023), which is hereby incorporated by reference in its entirety.

TECHNICAL FIELD

The present invention relates to a method for analyzing amino acids and/or acylcarnitines contained in an analyte sample.

BACKGROUND ART

Newborn screening tests have been widely carried out in order to detect and treat inborn errors of metabolism or similar abnormalities of newborns. In recent years, with the rapid progress of the technique of mass spectrometry, newborn mass-screening tests which use tandem mass spectrometers have been popularly conducted, contributing to the early detection of the inborn errors of metabolism of newborns (for example, see Non Patent Literature 1).

In the aforementioned type of newborn mass-screening test, a plurality of specific kinds of amino acids and acylcarnitines are respectively related to different diseases, and a cutoff value is set for each disease. For the screening of each disease, the amount and/or concentration of each of the specific kinds of amino acids and acylcarnitines contained in a sample derived from blood collected from a newborn is compared with the cutoff value corresponding to the substance concerned.

As disclosed in Non Patent Literature 1, in the screening process which uses a tandem mass spectrometer ("tandem mass-screening"), a multiple reaction monitoring (MRM) measurement using an MRM transition previously set for each of the specific kinds of amino acids and acylcarnitines is performed to determine the quantity of each of those substances, and each quantitative value is compared with the cutoff value.

CITATION LIST

Non Patent Literature

Non Patent Literature 1: Yousuke Shigematsu, "The Realities of Newborn Screening by Tandem Mass Spectrometry in Japan", *Journal of the Mass Spectrometry Society of Japan*, Vol. 64, No. 4, 2016, pp. 127-131

Non Patent Literature 2: Takao Ishikawa, Michiko Tezuka, Miwa Yoshinaga, Syosuke Nomachi, Nobuhito Hosomi, and Koichi Yano, "Influence of waxing on Leucine and Isoleucine Quantification for newborn screening using tandem mass spectrometry", *Japanese Journal of Neonatal Screening*, Vol. 30 (3), 2020, pp. 31 (257)-43 (269)

Non Patent Literature 3: Neiko Saito, Yoichi Wada, Masamitsu Maekawa, and Shigeo Kure, "Three cases that middle chain acyl-coenzyme A dehydrase deficiency became false-positive in neonates mass screening by essential oil", *Japanese Journal of Neonatal Screening*, Vol. 30 (2), 2020, p. 102 (196)

SUMMARY OF INVENTION

Technical Problem

In a newborn mass-screening test, a huge number of specimens ("analyte samples") must be quickly analyzed. Therefore, a flow injection analysis (FIA) method has been commonly used for the measurement, in which the samples set in an autosampler are sequentially introduced into a mass spectrometer along with a mobile phase, without being made to flow through a column in a liquid chromatograph (LC). In the flow injection analysis method, since each sample is introduced into the mass spectrometer without undergoing component separation by the column, various substances contained in the sample are simultaneously subjected to the MRM measurement.

For example, as described in Non Patent Literature 1, C5 acylcarnitines (a type of acylcarnitine having an acyl group with a carbon number of 5) include four isomers: isovalerylcarnitine, pivaloylcarnitine, 2-methylbutyrylcarnitine and n-valerylcarnitine. Among these isomers, isovalerylcarnitine and 2-methylbutyrylcarnitine are metabolites associated with specific diseases, whereas pivaloylcarnitine is a metabolite originating from a medicinal agent (antimicrobial agent) administered to newborns. Therefore, even when the quantitative value of C5 acylcarnitines in an MRM measurement has exceeded the cutoff value and the specimen has been tested positive by the screening, it may possibly be a false-positive case due to pivaloylcarnitine originating from a medicinal agent.

The previously described example is a false-positive case due to a substance originally contained in the analyte sample (intrinsic substance). A false-positive case can also occur due to a foreign substance mixed into a sample in the process of collecting or preparing the sample (extrinsic substance). For example, according to Non Patent Literature 2, a false-positive case occurs in the screening test for maple syrup urine disease if diethylene glycol monoethyl ether contained in a chemical agent used for waxing is mixed into the sample during its preparation and subjected to the measurement along with leucine and isoleucine. Furthermore, according to Non Patent Literature 3, a false-positive case occurs in the screening test for middle chain acyl-coenzyme A dehydrase (MCAD) deficiency if a component contained in an essential oil used in aroma therapy for a postpartum mother is mixed into the sample during its collection process and subjected to the measurement along with octanoylcarnitine (C8) or decanoylcarnitine (C10). Although those extrinsic substances are not isomers of the amino acids or acylcarnitines which are analysis targets, it is difficult for tandem quadrupole mass spectrometers, which are commonly used for newborn mass-screening tests, to discriminate between different ions having the same integer mass (mass-to-charge ratio), so that a false-positive case may possibly occur due to a substance having the same integer mass as an amino acid or acylcarnitine which is an analysis target.

Therefore, in a conventional screening test, when a sample has been tested positive, an additional test employing a different analyzing technique, such as chromatograph mass spectrometry using a column, is carried out to perform a detailed data analysis and determine the presence or absence of the disease concerned. Since a newborn screening test normally requires an analyte sample prepared from blood obtained from a newborn, performing an additional test as mentioned earlier will physically impose a heavy burden on the newborn. Having a positive case in the screening test will also psychologically put a heavy burden on the parents of the newborn. Furthermore, an increase in the number of false-positive cases means an increase in the number of samples requiring additional tests, which causes an increase in the workload of analysis operators and imposes a heavier burden on them. Accordingly, a technique for reducing the number of false-positive cases in the screening test has been in demand.

Although specific kinds of amino acids and acylcarnitines have been mentioned thus far to explain the problem with the conventional technique, a similar problem also occurs in the case of a screening test in which a measurement is performed for other kinds of amino acids or acylcarnitines.

The problem to be solved by the present invention is to improve the accuracy of the determination on whether or not a specific kind of amino acid or acylcarnitine is contained in an analyte sample in an analyzing method in which an MRM measurement of those substances is performed.

Solution to Problem

A first mode of the method for analyzing amino acids and/or acylcarnitines according to the present invention developed for solving the previously described problem includes:

- setting, for each of one or more target substances each of which is an amino acid or an acylcarnitine, a first MRM transition and a second MRM transition each of which is a combination of the mass-to-charge ratio of a precursor ion and the mass-to-charge ratio of a product ion, as well as a first reference value concerning a measured intensity of the first MRM transition and a second reference value concerning the ratio between the measured intensity of the first MRM transition and a measured intensity of the second MRM transition;
- measuring, for each of the target substances, a first intensity which is the measured intensity of the first MRM transition and a second intensity which is the measured intensity of the second MRM transition, by performing an MRM measurement of an analyte sample using the first MRM transition and the second MRM transition set for each of the target substances;
- performing, for each of the target substances, a first determination in which the value of the first intensity is compared with the first reference value to determine whether or not the target substance concerned is possibly contained in the analyte sample; and
- performing, for a target substance considered to be possibly contained in the analyte sample in the first determination, a second determination in which the ratio between the value of the first intensity and the value of the second intensity is compared with the second reference value to determine whether or not the target substance concerned is contained in the analyte sample.

A second mode of the method for analyzing amino acids and/or acylcarnitines according to the present invention developed for solving the previously described problem includes:

- setting, for each of one or more target substances each of which is an amino acid or an acylcarnitine, a first MRM transition which is a combination of the mass-to-charge ratio of a precursor ion and the mass-to-charge ratio of a product ion, a reference value concerning a measured intensity of the first MRM transition, as well as a second MRM transition with which a foreign substance that is detectable along with the target substance in an MRM measurement using the first MRM transition is undetectable;
- measuring, for each of the target substances, a first intensity which is the measured intensity of the first MRM transition and a second intensity which is the measured intensity of the second MRM transition, by performing an MRM measurement of an analyte sample using the first MRM transition and the second MRM transition set for each of the target substances;
- performing, for each of the target substances, a first determination in which the value of the first intensity is compared with the reference value to determine whether or not the target substance concerned is possibly contained in the analyte sample; and
- performing, for a target substance considered to be possibly contained in the analyte sample in the first determination, a second determination in which whether or not the target substance is contained in the analyte sample is determined based on the value of the second intensity.

Advantageous Effects of Invention

In the first and second modes of the present invention, a first MRM transition, a second MRM transition, and a reference value (or a first reference value in the first mode) concerning a measured intensity of the first MRM transition are set for each of one or more target substances each of which is an amino acid or acylcarnitine. An MRM measurement of an analyte sample is performed using the first and second MRM transitions for each target substance. The first MRM transition may be set so that it enables a highly sensitive measurement of the target substance, like the MRM transition used in the conventional mass-screening. The reference value (the same as above) concerning a measured intensity of the first MRM transition may also be set so that it corresponds to the cutoff value used in the conventional mass-screening.

In the first and second modes of the present invention, initially, for each target substance, a measured intensity obtained with the first MRM transition is compared with a reference value to determine the possibility that the target substance is contained in the analyte sample (first determination). Conventional mass-screening simply relies on this determination when determining the possibility that the target substance is contained in the analyte sample. Therefore, it has been impossible to discriminate between the case where the target substance is actually contained in the analyte sample and the case where the target substance is not contained and what is actually present is only an isomer or similar foreign substance that can be detected along with the target substance when the first MRM transition is used.

In the first mode of the present invention, a second reference value is set which concerns the ratio between a measured intensity of the first MRM transition and a measured intensity of the second MRM transition. For a target substance which has been considered to be possibly contained in the analyte sample (first determination), the ratio between the first intensity value and the second intensity value is additionally compared with the second reference value to determine whether or not the target substance is contained in the analyte sample (second determination). Even when a foreign substance that can be detected along with the target substance when the first MRM transition is used is present, there is normally a certain difference between the target substance and the foreign substance in terms of the value of the ratio between the intensity measured by the first MRM transition and the intensity measured by the second MRM transition. In the first mode of the present invention, when the first determination indicates that the target substance is possibly contained, the aforementioned ratio is compared with the second reference value to determine whether or not the substance contained in the analyte sample is the target substance or a foreign substance (second determination). Therefore, whether or not the target substance is contained in the analyte sample can be determined more accurately than ever before.

In the second mode of the present invention, a second MRM transition is set which is an MRM transition with which the foreign substance that is detectable along with the target substance concerned in the MRM measurement using the first MRM transition is undetectable. For each target substance considered to be possibly contained in the analyte sample in the first determination, whether or not the target substance concerned is contained in the analyte sample is determined based on the value of a measured intensity (second intensity value) obtained by the second MRM transition (second determination). In the second mode of the present invention, the determination that the target substance is contained in the analyte sample (second determination) is made based on the condition where the target substance is detected in the MRM measurement using the second MRM transition with which the foreign substance is undetectable. Therefore, whether or not the target substance is contained in the analyte sample can be determined more accurately than ever before.

BRIEF DESCRIPTION OF DRAWINGS

FIG. 2 is one example of a compound database in the present embodiment.

FIG. 3 is a diagram illustrating a first analysis mode of the present embodiment.

FIG. 5 is still another diagram illustrating the first analysis mode of the present embodiment.

FIG. 6 is a diagram illustrating a second analysis mode of the present embodiment.

FIG. 7 is another diagram illustrating the second analysis mode of the present embodiment.

FIG. 8 is still another diagram illustrating the second analysis mode of the present embodiment.

DESCRIPTION OF EMBODIMENTS

One embodiment of the method for analyzing amino acids and/or acylcarnitines according to the present invention is hereinafter described with reference to the drawings. The method for analyzing amino acids and/or acylcarnitines according to the present embodiment may be used for carrying out a newborn mass-screening test, for example.

Figure 1:
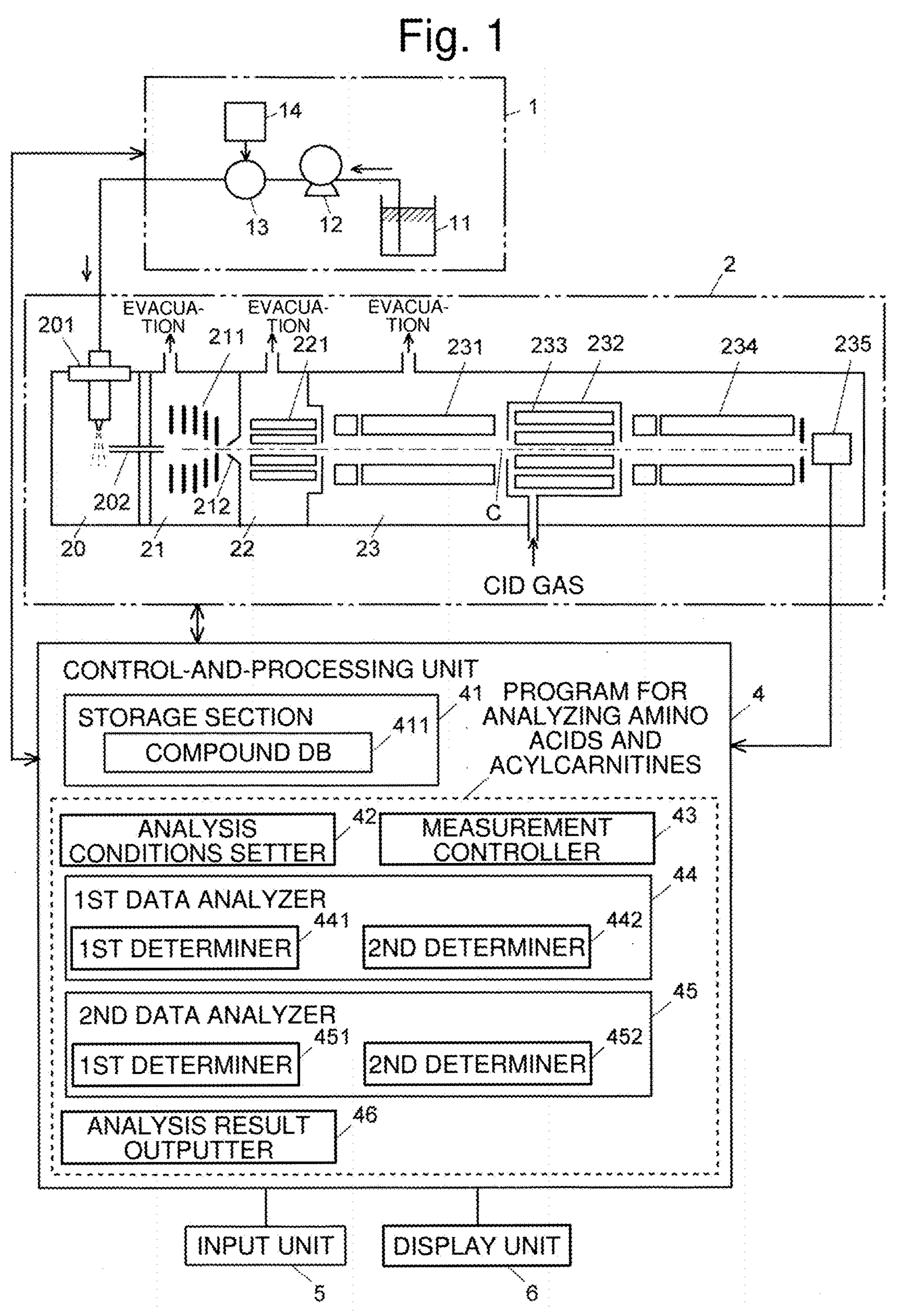
FIG. 1 is a configuration diagram of the main components of a liquid chromatograph mass spectrometer used in one embodiment of the method for analyzing amino acids and/or acylcarnitines according to the present invention.

FIG. 1 is a configuration diagram of the main components of a liquid chromatograph mass spectrometer used in the present embodiment. The liquid chromatograph mass spectrometer in the present embodiment includes a liquid chromatograph 1, a mass analyzer 2 and a control-and-processing unit 4 for controlling the operations of these devices.

The liquid chromatograph 1 includes: a mobile phase container 11 in which a mobile phase is stored; a pump 12 for drawing the mobile phase (solvent) and supplying it at a constant flow rate; an injector 13 for injecting a liquid sample into the mobile phase; and an autosampler 14 connected to the injector 13. Although the liquid chromatograph 1 includes a column for separating components in a sample, this column is not used in the present embodiment; the liquid sample is introduced into the mass analyzer 2 along with the mobile phase by the flow injection analysis (FIA) method.

The mass analyzer 2 includes an ionization chamber 20 maintained at substantially atmospheric pressure and a vacuum chamber connected to the ionization chamber 20. The vacuum chamber is evacuated by means of vacuum pumps (not shown). The vacuum chamber internally has a first intermediate vacuum chamber 21, second intermediate vacuum chamber 22 and analysis chamber 23 sequentially arranged from the ionization chamber 20, having the configuration of a multi-stage differential pumping system in which the degrees of vacuum in those chambers are sequentially increased in the mentioned order.

The ionization chamber 20 is provided with an electrospray ionization (ESI) probe 201 configured to spray a sample liquid while imparting electric charges to the same liquid. The ionization chamber 20 communicates with the first intermediate vacuum chamber 21 in the subsequent stage through a thin heated capillary (desolvation tube) 202.

The first intermediate vacuum chamber 21 contains an ion lens 211 formed by a plurality of ring electrodes. The ion lens 211 is configured to converge the flight path of the ions along the ion beam axis C (the central axis of the flight direction of the ions). The first intermediate vacuum chamber 21 is separated from the second intermediate vacuum chamber 22 by a skimmer 212 having a small hole at its apex.

The second intermediate vacuum chamber 22 contains an ion guide 221 formed by a plurality of rod electrodes. Similar to the ion lens 211, the ion guide 221 is configured to converge the flight path of the ions along the ion beam axis C. The second intermediate vacuum chamber 22 is separated from the analysis chamber 23 by a partition wall in which a small hole is formed.

Within the analysis chamber 23, a front quadrupole mass filter 231, collision cell 232, rear quadrupole mass filter 234 and ion detector 235 are arranged. An ion guide 233 is located within the collision cell 232. A collision-induced dissociation (CID) gas is introduced from a gas source (not shown) into the collision cell 232.

The mass analyzer 2 can perform various measurements, including a selected ion monitoring (SIM) measurement, MS/MS scan (product-ion scan) measurement and multiple reaction monitoring (MRM) measurement. In the SIM measurement, no selection of ions is performed in the front quadrupole mass filter 231 (this filter is not operated as a mass filter), while the mass-to-charge ratio at which ions are allowed to pass through and be detected is fixed in the rear quadrupole mass filter 234.

In the MS/MS scan measurement and the MRM measurement, both of the front and rear quadrupole mass filters 231 and 234 are operated as mass filters. In the front quadrupole mass filter 231, only an ion having a mass-to-charge ratio designated as a precursor ion is allowed to pass through. Meanwhile, a CID gas is supplied into the collision cell 232, and the precursor ion is accelerated into the inner space of this cell in order to promote fragmentation of the precursor ion through the collision of the precursor ion with the CID gas. In the case of the MS/MS scan measurement, the mass-to-charge ratio at which ions are allowed to pass through the rear quadrupole mass filter 234 is continuously varied for mass scan. In the case of the MRM measurement, the mass-to-charge ratio at which ions are allowed to pass through the rear quadrupole mass filter 234 is fixed so that only a product ion having a specific mass-to-charge ratio is allowed to pass through.

The control-and-processing unit 4 has a storage section 41. In the storage section 41, a compound database (DB) 411 which holds information including the measurement conditions and analyzing methods for a plurality of known amino acids and acylcarnitines is previously stored (preliminary step: Step 0; see FIG. 9). FIG. 2 shows one example of the items of information stored in the compound database 411. For example, the measurement conditions recorded in the compound database 411 include: the compound name; the magnitude of the collision energy in the measurement of the compound; the mass-to-charge ratios of the target MRM transition to be used for the first determination in the first and second analysis modes (which will be described later); the reference value of the measured intensity of the ion by the target MRM transition; the mass-to-charge ratios of the qualifier MRM transition to be used in the first analysis mode (first analysis qualifier MRM transition); the reference value concerning the ratio of the measured intensity of the ion by the first analysis qualifier MRM transition to the measured intensity of the ion by the target MRM transition; the mass-to-charge ratios of the qualifier MRM transition to be used in the second analysis mode (second analysis qualifier MRM transition); and the information of the threshold of the measured intensity of the ion by the second analysis qualifier MRM transition. The measured intensity of the ion by the target MRM transition, the ratio of the aforementioned measured intensities, and the measured intensity of the ion by the second analysis qualifier MRM transition individually serve as indices in a newborn mass-screening test. The storage section 41 also holds information which relates each compound to a specific disease associated with that compound.

Examples of the amino acids to be recorded in the compound database 411 include phenylalanine, leucine, isoleucine, methionine, citrulline and tyrosine. Examples of the acylcarnitines to be recorded in the compound database 411 include free carnitine (C0), acetylcarnitine (C2), propionylcarnitine (C3), butyrylcarnitine-palmitoylcarnitine (C4-C18), isovalerylcarnitine, 2-methylbutyrylcarnitine, pivaloylcarnitine (C5), tiglylcarnitine (C5:1), glutarylcarnitine (C5-DC), 3-hydroxyisovalerylcarnitine, 3-hydroxy-2-methylbutyrylcarnitine (C5-OH), octanoylcarnitine (C8), decanoylcarnitine (C10), dodecanoylcarnitine (C12), tetradecenoylcarnitine (C14:1), tetradecanoylcarnitine (C14), palmitoylcarnitine (C16), stearylcarnitine (C18), octadecenoylcarnitine (C18:1), hydroxyhexadecanoylcarnitine (C16-OH) and hydroxyoctadecenoylcarnitine (C18:1-OH).

Each of the aforementioned MRM transitions is a combination of the mass-to-charge ratio of a precursor ion generated from the compound concerned (amino acid or acylcarnitine) and that of a product ion resulting from the fragmentation of the precursor ion. That is to say, an MRM measurement includes the following steps: An ion having the mass-to-charge ratio of the precursor ion specified in the MRM transition is selected by the front quadrupole mass filter 231. The selected ion is fragmented into product ions in the collision cell 232. From those product ions, an ion having the mass-to-charge ratio of the product ion specified in the MRM transition is selected by the rear quadrupole mass filter 234 and ultimately detected by the ion detector 235. As for the target MRM transition, an MRM transition with which the compound concerned (amino acid or acylcarnitine) can be detected with the highest level of sensitivity is normally selected.

As for the first analysis qualifier MRM transition, for example, an MRM transition which yields the highest measurement sensitivity second to the target MRM transition is selected. The first analysis qualifier MRM transition has a corresponding reference value of a score concerning the ratio of the measured intensity of the first analysis qualifier MRM transition to that of the target MRM transition. In the first analysis mode, the measured intensity of the ion by the target MRM transition becomes the first index value, and the aforementioned score becomes the second index value.

As for the second analysis qualifier MRM transition, an MRM transition which cannot be generated from any (foreign) compound that is detectable along with the compound concerned in the measurement using the target MRM transition is selected. The second analysis qualifier MRM transition has the information of a corresponding threshold of the measured intensity of the second analysis qualifier MRM transition. For example, this threshold is set at a value distinguishable from noise components. The threshold may be set at a value of zero when there is no need to consider noise components. In the second analysis mode, the measured intensity of the ion by the target MRM transition becomes the first index value, while that of the second analysis qualifier MRM transition becomes the second index value in the newborn mass-screening test.

The control-and-processing unit 4 includes, as its functional blocks, an analysis condition setter 42, measurement controller 43, first data analyzer 44, second data analyzer 45 and analysis result outputter 46. The first data analyzer 44 includes a first determiner 441 and a second determiner 442. Similarly, the second data analyzer 45 also includes a first determiner 451 and a second determiner 452. The control-and-processing unit 4 is actually a personal computer, on which each functional block is embodied by executing, on the processor in the computer, a pre-installed program for analyzing amino acids and acylcarnitines. Additionally, an input unit 5 and a display unit 6 are connected to the control-and-processing unit 4.

A specific example of the qualifier MRM transition to be used in the first analysis mode (first analysis qualifier MRM transition) and that of the qualifier MRM transition to be used in the second analysis mode (second analysis qualifier MRM transition) are hereinafter described.

The first analysis mode can be suitably used, for example, in the case of analyzing isovalerylcarnitine having a molecular structure as shown in FIG. 3. Isovalerylcarnitine is a substance usable as a marker of isovaleric acidemia. Its isomers include pivaloylcarnitine, which is a metabolite originating from an antimicrobial agent that may be administered to newborns. The mass-to-charge ratio of the hydrogen-adduction ($[M+H]^+$) of isovalerylcarnitine is 246.15 (or 246 in integer mass). The target MRM transition which yields the highest measurement sensitivity for isovalerylcarnitine is 246.15>84.95 (an MRM transition for detecting a product ion having a mass-to-charge ratio of 84.95 generated from a precursor ion having a mass-to-charge ratio of 246.15; 246>85 in integer mass). However, a product ion of the same MRM transition can also be generated from pivaloylcarnitine. Therefore, a liquid sample which contains only pivaloylcarnitine will also be tested positive (false-positive) in a screening test which uses only the target MRM transition.

Figure 4:
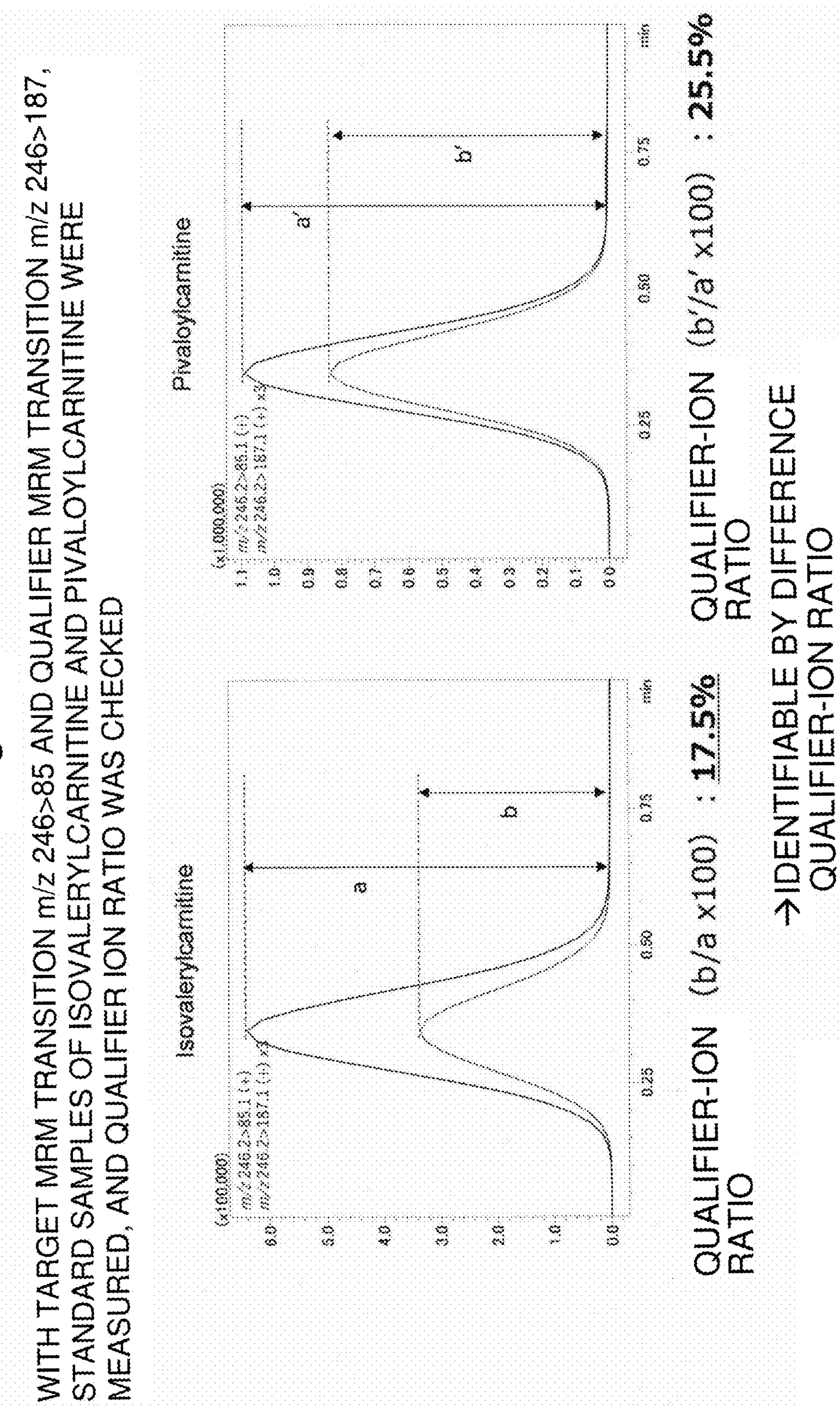
FIG. 4 is another diagram illustrating the first analysis mode of the present embodiment.

In the first analysis mode, in addition to the target MRM transition, an MRM measurement using the first analysis qualifier MRM transition (246.15>187.05, or 246>187 in integer mass) is also performed, and the ratio of the measured intensity (i.e., either the height or the area of a mass-chromatogram peak; the same applies hereinafter) of the first analysis qualifier MRM transition to that of the target MRM transition is calculated. As shown in FIG. 4, this measured-intensity ratio for isovalerylcarnitine is 17.5%, while the ratio for pivaloylcarnitine is 25.5%; there is a sufficient difference for discriminating between the two substances. Accordingly, in the first analysis mode, the measured-intensity ratio calculated from the measurements of the actual liquid sample is compared with the value of the measured-intensity ratio of isovalerylcarnitine to determine whether the substance contained in the liquid sample is isovalerylcarnitine or pivaloylcarnitine.

The previously described determination may be made by directly comparing the value of the measured-intensity ratio obtained by the measurement of an actual sample with the value of the measured-intensity ratio obtained by the measurement of a standard sample of the target substance. However, in that case, the value changes depending on the compound as well as on the used qualifier MRM transition. Therefore, it is preferable to use an index common to all target substances as well as to all qualifier MRM transitions, rather than to determine whether or not the substance concerned is the target substance based on the value of the difference between the reference value of the measured-intensity ratio and the value of the measured-intensity ratio calculated from the measurements of an actual sample. Accordingly, for example, the following equation (1) may preferably be used to calculate a score value from the value of the measured-intensity ratio, with a score value of 100 representing the perfect matching. The score value calculated in this manner allows the determination to be made using the same criterion for all compounds.

$$\text{Score} = 100 - \Big( \big| (\text{Value of measured-intensity ratio of actual sample}) - (\text{Reference value of measured-intensity ratio}) \big| \,/\, (\text{Reference value of measured-intensity ratio}) \times 100 \Big) \quad (1)$$

FIG. 5 shows an example of the determination based on the score value. This is an example of the discrimination between isovalerylcarnitine, which is the target substance, and a foreign substance, such as pivaloylcarnitine. The measured-intensity ratio of the first analysis qualifier MRM transition to that of the target MRM transition, as calculated from a standard sample of isovalerylcarnitine, is 20.44%. (It should be noted that the value of the measured-intensity ratio is different from the value shown in FIG. 4 since the MRM transition used as the first analysis qualifier MRM transition in the present case is different from the one used in the example described in FIG. 4.) Consider the case where the values of the measured-intensity ratio of the first analysis qualifier MRM transition to that of the target MRM transition, calculated for two specimens ("Specimens 1 and 2") which are actual samples, are 20.48% (Specimen 1) and 28.21% (Specimen 2), respectively. In this case, the score values calculated from those numerical values and the aforementioned equation (1) are 99.78% for Specimen 1 and 61.99% for Specimen 2. The reference value of the score (the cutoff value of the index value) may be set at 75, for example, in which case it is possible to conclude that Specimen 1 contains isovalerylcarnitine, while Specimen 2 does not contain isovalerylcarnitine. This reference value can be appropriately set according to the purpose of the screening, required level of accuracy and other related factors. For example, a comparatively low reference value can be set in the case of a screening test in which no positive case should be missed. As a specific example, the reference value of the score may be an appropriate value within a range from 70 to 80, inclusive.

The second analysis mode can be suitably used, for example, in the case of analyzing glutarylcarnitine (C5-DC) having a molecular structure as shown in FIG. 6. Glutarylcarnitine is a marker substance for glutaric acidemia type I. It has a mass-to-charge ratio of 275.14 (or 275 in integer mass). For glutarylcarnitine, there is an acylcarnitine having the same integer mass and a different composition: hydroxyhexanoylcarnitine (C6-OH, which has a mass-to-charge ratio of 275.17, or an integer mass of 275). For newborn mass-screening tests, tandem quadrupole mass spectrometers are often used, and it is difficult to for this type of mass spectrometer to discriminate between substances having the same integer mass.

Accordingly, in the second analysis mode, an MRM transition with which a product ion is generated from glutarylcarnitine as the target substance while no product ion is generated from hydroxyhexanoylcarnitine is used as a qualifier MRM transition (second analysis qualifier MRM transition).

Figure 7:
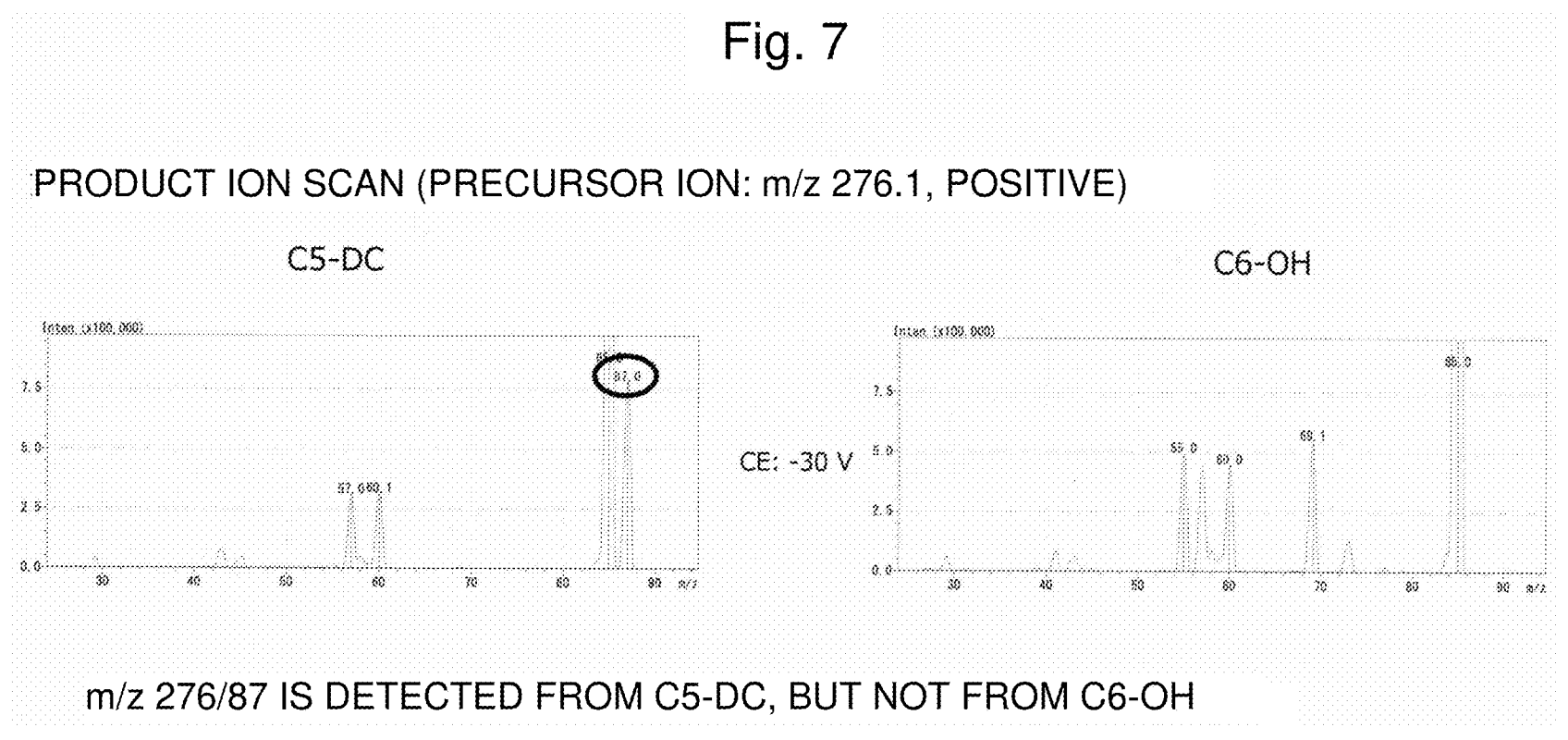

FIG. 7 shows product-ion spectra (positive ion mode, with the precursor ion having a mass-to-charge ratio of 276.1) for glutarylcarnitine (C5-DC) and hydroxyhexanoylcarnitine (C6-OH). A comparison of those product-ion spectra shows that a product ion having a mass-to-charge ratio of 87.0 is detected from glutarylcarnitine with a high level of intensity, while no product ion having a mass-to-charge ratio of 87.0 is detected from hydroxyhexanoylcarnitine. FIG. 8 shows mass chromatograms acquired by performing MRM measurements for each of the standard samples of glutarylcarnitine and hydroxyhexanoylcarnitine using the target MRM transition (276.1>85.0) which yields the highest measurement intensity for glutarylcarnitine and the aforementioned MRM transition (276.1>87.1). It can be seen that the product ion was detected from both substances in the case of the target MRM transition (276.1>85.0), whereas only glutarylcarnitine was detected in the case of the aforementioned MRM transition (276.1>87.1). Accordingly, it is possible to determine whether the substance contained in the specimen is glutarylcarnitine or hydroxyhexanoylcarnitine by using 276.1>87.1 as the second analysis qualifier MRM transition. In the present example, it is still possible to perform the measurement of glutarylcarnitine by an MRM measurement which uses only the second analysis qualifier MRM transition. However, this type of MRM transition does not always yield a high level of measurement sensitivity. Therefore, in the second analysis mode, a determination which uses the target MRM transition that yields a high level of measurement sensitivity is initially performed, followed by an additional determination which uses the second analysis qualifier MRM transition.

Figure 9:
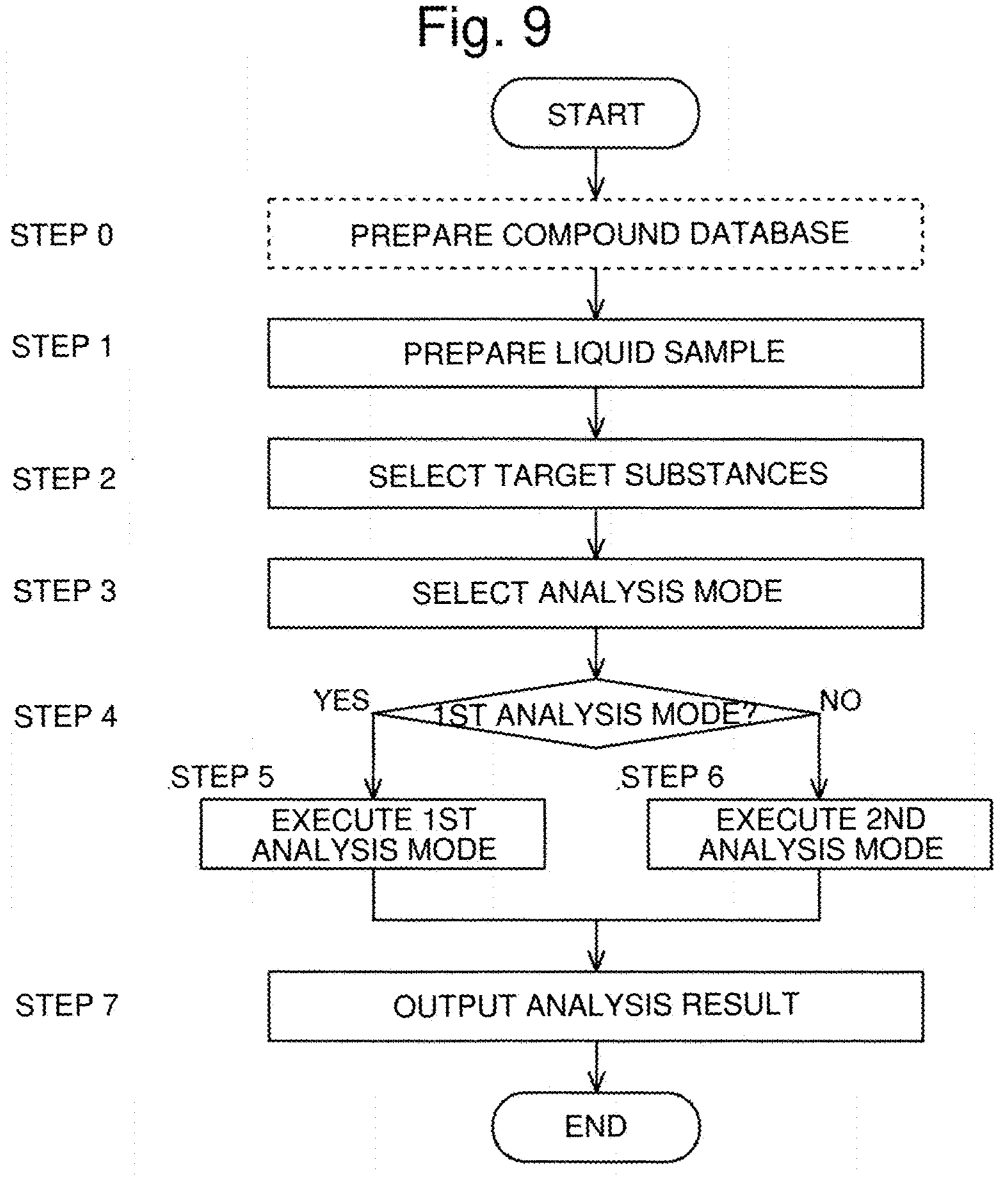
FIG. 9 is a flowchart illustrating the procedure of the method for analyzing amino acids and/or acylcarnitines according to the present embodiment.
Figure 10:
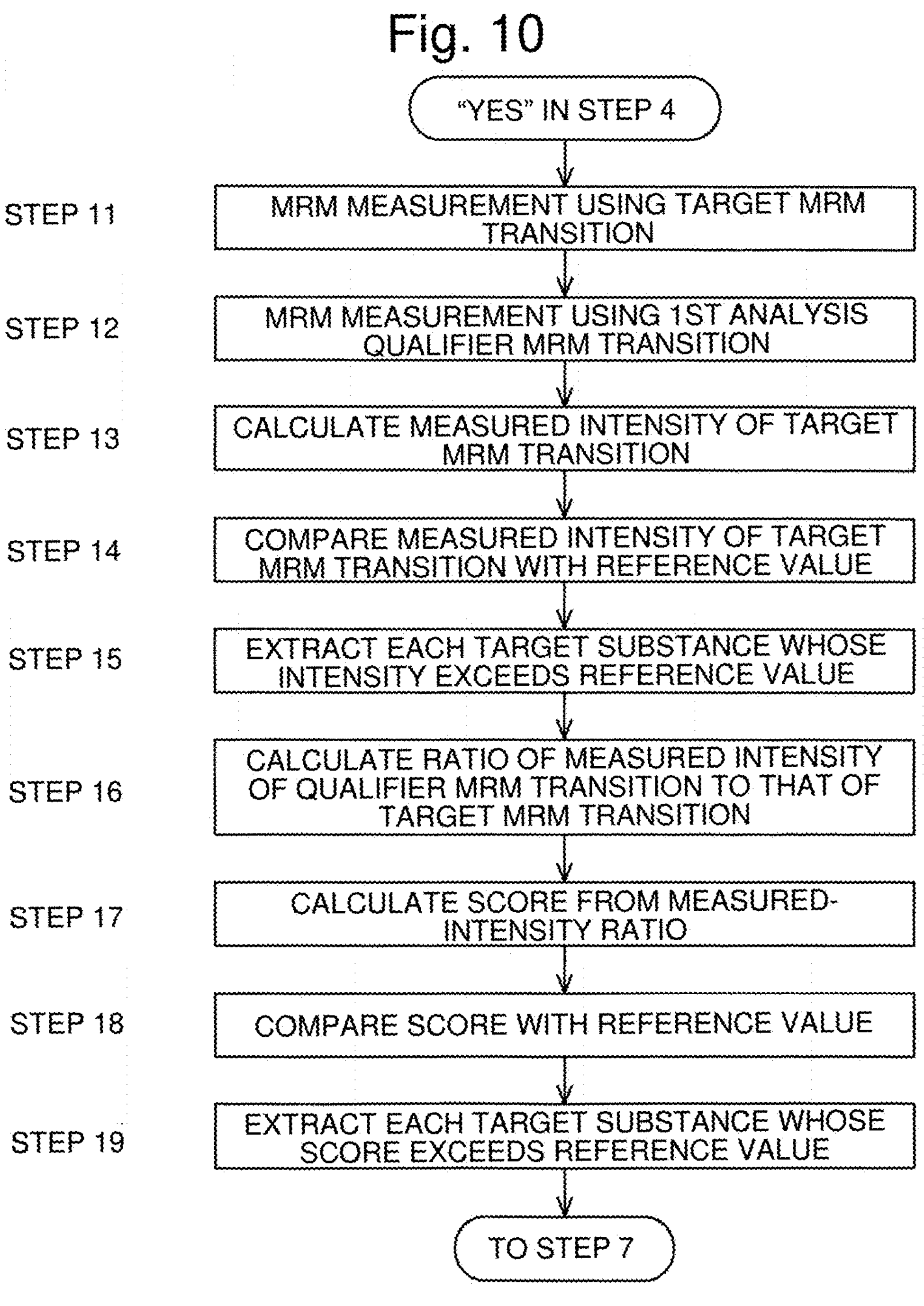
FIG. 10 is a flowchart illustrating the procedure of the first analysis mode in the method for analyzing amino acids and/or acylcarnitines according to the present embodiment.
Figure 11:
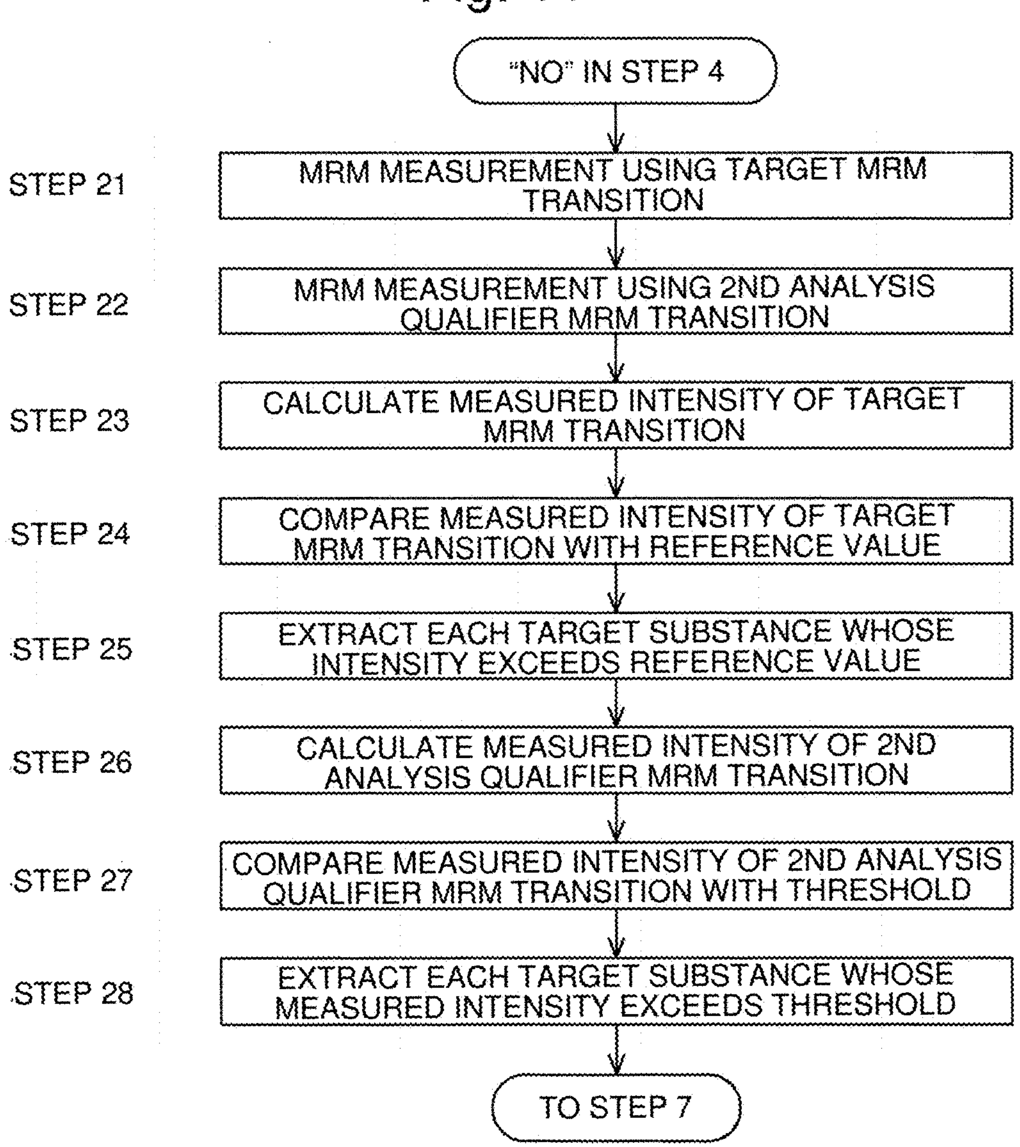
FIG. 11 is a flowchart illustrating the procedure of the second analysis mode in the method for analyzing amino acids and/or acylcarnitines according to the present embodiment.

Hereinafter, a procedure for analyzing amino acids and acylcarnitines contained in a liquid sample to be analyzed using the liquid chromatograph mass spectrometer according to the present embodiment is described with reference to FIGS. 9-11. FIG. 9 is a flowchart showing the general flow of the analyzing method according to the present embodiment.

Initially, a specimen (blood) is collected from each newborn as a subject, and a liquid sample is prepared from the specimen (Step 1). For example, the preparation of the liquid sample (collection of amino acids and acylcarnitines) can be carried out by performing an extracting operation using water and ethanol on a piece of filter paper on which a blood specimen collected from a newborn is put, as described in Non Patent Literature 1. The prepared liquid samples are set in the autosampler 14.

After the liquid samples have been set in the autosampler 14, the user issues a command to initiate the analysis. Then, the analysis condition setter 42 displays a screen for setting analysis conditions on the display unit 6. This screen shows a list of amino acids and acylcarnitines recorded in the compound database 411. The user selects compounds to be analyzed (target substances) from the list (Step 2). The screen may alternatively or additionally be configured to allow the user to collectively select a set of previously grouped compounds (e.g., a group of target compounds for newborn mass-screening tests).

After the target substances have been selected, the analysis condition setter 42 prompts the user to select either the first or second analysis mode (Step 3). The following description initially deals with the case where the first analysis mode has been selected.

When the first analysis mode is selected (YES in Step 4), the first analysis mode is executed by the following procedure (Step 5). FIG. 10 is a flowchart showing the process flow in the first analysis mode of the present embodiment.

The analysis condition setter 42 reads, from the compound database 411, the target MRM transition and the first analysis qualifier MRM transition for each target substance and prepares a method file which describes a method for sequentially executing those MRM transitions for their respective predetermined periods of time. The analysis condition setter 42 also prepares a batch file for performing a measurement of each liquid sample set in the autosampler 14 using that method and saves that file in the storage section 41.

After the batch file has been prepared, the user issues a command to initiate the measurement. Then, the measurement controller 43 operates the autosampler 14 to inject one of the liquid samples into the injector 13. The liquid sample injected into the injector 13 is introduced into the ESI probe 201 along with the mobile phase by the FIA method.

The liquid sample introduced into the ESI probe 201 is ionized within the ionization chamber 20. The resulting ions are transported to the front quadrupole mass filter 231, being converged along the ion beam axis C by the ion lens 211 in the first intermediate vacuum chamber 21 as well as the ion guide 221 in the second intermediate vacuum chamber 22. The front quadrupole mass filter 231 selects, as a precursor ion, an ion having a mass-to-charge ratio specified in the target MRM transition for the first target substance. The precursor ion selected by the front quadrupole mass filter 231 undergoes dissociation within the collision cell 232 due to the collision with the CID gas molecule. The resulting ions enter the rear quadrupole mass filter 234. The rear quadrupole mass filter 234 selects, as a product ion, an ion having a mass-to-charge ratio specified in the target MRM transition for the first target substance. The ion selected by the rear quadrupole mass filter 234 subsequently enters the ion detector 235 and is thereby detected (Step 11). The ion detector 235 detects ions for a predetermined period of time and sends signal data corresponding to the intensity of the ions to the control-and-processing unit 4. The control-and-processing unit 4 receives the signal data from the ion detector 235 and sequentially saves them in the storage section 41.

After the measurement of the target MRM transition for the first target substance has been completed, a similar measurement is performed for the first analysis qualifier MRM transition for the same substance (Step 12). When the measurements using the target MRM transition and the first analysis qualifier MRM transition have been completed for all target substances, the measurement of the first liquid sample is over.

After the measurement of the first liquid sample has been completed, the measurement of the second liquid sample is performed in a similar manner, using the target MRM transition and the first analysis qualifier MRM transition for each target substance. The entire measurement operation is over when the measurements for all liquid samples have been completed.

After the completion of the entire measurement (or concurrently with the measurement operation), the first data analyzer 44 in the control-and-processing unit 4 initially creates, for each target substance in the first liquid sample, a mass chromatogram showing measurement data for the target MRM transition and calculates the height (or the area; the same applies hereinafter) of the peak in that chromatogram (Step 13). After the peak height has been calculated for all target substances, the first determiner 441 reads, from the compound database 411, the thresholds (Tta, Ttb, Ttc, . . . ) respectively specified for the target substances and compares the peak-height value of the mass chromatogram of each target substance with the corresponding threshold (Step 14), to extract each target substance whose peak-height value exceeds the threshold (Step 15).

Next, for each target substance extracted by the first determiner 441, the first data analyzer 44 creates a mass chromatogram showing measurement data for the first analysis qualifier MRM transition, determines the height of the peak in that chromatogram, and calculates the ratio to the peak-height value of the target MRM transition (Step 16). After the calculation of the ratio of the peak-height value has been completed for all target substances extracted by the first determiner 441, the second determiner 442 reads, from the compound database 411, the reference values (Ra, Rb, Rc, . . . ) for the peak-height ratio (measured-intensity ratio) respectively specified for the target substances and calculates the score for each target substance by the aforementioned equation (1) (Step 17), to compare the score value of each target substance with the corresponding reference value (Step 18) and extract each target substance whose score value exceeds the reference value (Step 19).

After the sequential processes described thus far have been completed for all liquid samples, the analysis result outputter 46 displays, on the screen of the display unit 6, a list of liquid samples from which target substances have been extracted by the second determiner 442, with each liquid sample related to a target substance or substances extracted by the second determiner 442, and each target substance related to the name of the corresponding disease ("Output Analysis Result"; Step 7).

Next, the case where the second analysis mode has been selected by the user is described. When the second analysis mode is selected (NO in Step 4), the second analysis mode is executed by the following procedure (Step 6). FIG. 11 is a flowchart showing the process flow in the second analysis mode of the present embodiment.

The analysis condition setter 42 reads, from the compound database 411, the target MRM transition and the second analysis qualifier MRM transition for each target substance and prepares a method file which describes a method for sequentially executing those MRM transitions for their respective predetermined periods of time. The analysis condition setter 42 also prepares a batch file for performing a measurement of each liquid sample set in the autosampler 14 using that method and saves that file in the storage section 41.

After the batch file has been prepared, the user issues a command to initiate the measurement. Then, the measurement controller 43 operates the autosampler 14 to inject one of the liquid samples into the injector 13. The liquid sample injected into the injector 13 is introduced into the ESI probe 201 along with the mobile phase by the FIA method, to be subjected to the mass spectrometric analysis. The procedure of the mass spectrometric analysis is similar to the case where the first analysis mode is selected: The MRM measurement using the target MRM transition is initially performed (Step 21), followed by the MRM measurement using the qualifier MRM transition (Step 22). (It should be noted that the second analysis mode uses the second analysis qualifier MRM transition in place of the first analysis qualifier MRM transition.) The steps of these measurements are similar to the corresponding steps in the first analysis mode. Therefore, detailed descriptions of those steps will be omitted.

After the completion of the measurements of all samples (or in parallel with the measurement operation), the second data analyzer 45 in the control-and-processing unit 4 initially creates, for each target substance in the first liquid sample, a mass chromatogram showing measurement data for the target MRM transition and calculates the height of the peak in that chromatogram (Step 23). After the peak height has been calculated for all target substances, the first determiner 451 reads, from the compound database 411, the thresholds (Tta, Ttb, Ttc, . . . ) respectively specified for the target substances and compares the peak-height value of the mass chromatogram of the target MRM transition of each target substance with the corresponding threshold (Step 24), to extract each target substance whose peak-height value exceeds the threshold (Step 25).

Next, for each target substance extracted by the first determiner 451, the second data analyzer 45 creates a mass chromatogram showing measurement data for the second analysis qualifier MRM transition and determines the height of the peak in that chromatogram (Step 26). After the calculation of the peak height has been completed for all target substances extracted by the first determiner 451, the second determiner 452 reads, from the compound database 411, the peak-height thresholds (Tqa, Tqb, Tqc, . . . ) respectively specified for the target substances and compares the peak-height value of the mass chromatogram of the second analysis qualifier MRM transition of each target substance with the corresponding threshold (Step 27), to extract each target substance whose peak-height value exceeds the threshold (Step 28).

After the sequential processes described thus far have been completed for all liquid samples, the analysis result outputter 46 displays, on the screen of the display unit 6, a list of liquid samples from which target substances have been extracted by the second determiner 452, with each liquid sample related to a target substance or substances extracted by the second determiner 452, and each target substance related to the name of the corresponding disease ("Output Analysis Result"; Step 7).

In the present embodiment, as described thus far, in both of the first and second analysis modes, a measured intensity obtained with the target MRM transition for each target substance is initially compared with a threshold to determine the possibility that the target substance is contained in the liquid sample (first determination). Conventional mass-screening simply relies on this determination when determining the possibility that the target substance is contained in the analyte sample. Therefore, it has been impossible to discriminate between the case where the target substance is actually contained in the analyte sample and the case where the target substance is not contained and what is actually present is only an isomer or similar foreign substance that can be detected along with the target substance when the first MRM transition is used.

In the first analysis mode of the present embodiment, a threshold is set which concerns the ratio between the peak-height value (measured intensity) of a mass chromatogram of the target MRM transition and the peak-height value (measured intensity) of a mass chromatogram of the first analysis qualifier MRM transition. For a target substance whose peak-height value has exceeded the threshold, i.e., which is possibly contained in the liquid sample (first determination), the ratio of the peak-height value of the mass chromatogram of the first analysis qualifier MRM transition to the peak-height value of the mass chromatogram of the target MRM transition is additionally compared with another threshold to further determine whether or not the target substance is contained in the liquid sample (second determination). Even when a foreign substance that can be detected along with the target substance in the measurement using the target MRM transition is present, there is normally a significant difference between the target substance and the foreign substance in terms of the value of the ratio between the intensity measured by the target MRM transition and the intensity measured by the first analysis qualifier MRM transition. In the first analysis mode of the present embodiment, when the result of the first determination indicates that the target substance is possibly contained, the aforementioned ratio is compared with the threshold to further determine whether the substance contained in the liquid sample is the target substance or a foreign substance (second determination). Therefore, whether or not the target substance is contained in the liquid sample can be determined more accurately than ever before.

In the second analysis mode of the present embodiment, a second analysis qualifier MRM transition is set which is an MRM transition with which the foreign substance that is detectable along with the target substance concerned in the MRM measurement using the target MRM transition is undetectable. For each target substance considered to be possibly contained in the liquid sample in the first determination, a second determination is performed in which whether or not the target substance concerned is contained in the liquid sample is further determined based on the peak-height value (measured intensity) of the mass chromatogram of the second analysis qualifier MRM transition. In the second analysis mode of the present embodiment, the determination that the target substance is contained in the liquid sample (second determination) is made once more based on the condition where the target substance is detected in the MRM measurement using the second analysis qualifier MRM transition with which the foreign substance is undetectable. Therefore, whether or not the target substance is contained in the liquid sample can be determined more accurately than ever before.

The previously described embodiment is a mere example and can be appropriately changed or modified without departing from the spirit of the present invention. In the previously described embodiment, samples are introduced into the mass analyzer 2 by the FIA method, without using a column, in order to enhance the measurement efficiency on the assumption that a huge number of specimens (samples) are to be analyzed. In other cases, e.g., when there are only a small number of specimens, a column may be used to separate the components in the sample before introducing the sample into the mass analyzer 2. Separating the substances contained in the analyte sample by a column before the MRM measurement makes it possible to more accurately determine whether or not the target substance is contained in the sample.

In the previously described embodiment, a liquid chromatograph mass spectrometer is used on the assumption that the autosampler 14 provided in the liquid chromatograph 1 should be used. It is also possible to directly introduce samples into the ESI probe 201 of the mass analyzer 2, in which case the liquid chromatograph 1 may be omitted. A gas chromatograph may be used in place of the liquid chromatograph, depending on the nature of the samples to be analyzed.

In the previously described embodiment, the user is prompted to manually select either the first or second analysis mode. Alternatively, or additionally, the compound database 411 may include information which relates each compound to an analysis mode so that the analysis mode can be automatically determined depending on the compound (target substance) selected by the user. As opposed to the previously described embodiment in which either the first or second analysis mode is selected, the system may also be configured to execute both analysis modes.

In the example shown in the previously described embodiment, one first analysis qualifier MRM transition and one second analysis qualifier MRM transition are recorded for each compound in the compound database 411 (FIG. 2). Two or more MRM transitions may also be set for one or both of the two qualifier MRM transitions. In that case, a reference value of the score concerning the measured-intensity ratio should be set for each of the plurality of first analysis qualifier MRM transitions. As for the plurality of second analysis qualifier MRM transitions, a threshold may be set for each MRM transition, or a common threshold may be set. The first and second analysis qualifier MRM transitions may be identical to or different from each other.

[Modes]

It is evident to a person skilled in the art that the previously described illustrative embodiment is a specific example of the following modes of the present invention.

(Clause 1)

A method for analyzing amino acids and/or acylcarnitines according to one mode of the present invention includes:

setting, for each of one or more target substances each of which is an amino acid or an acylcarnitine, a first MRM transition and a second MRM transition each of which is a combination of the mass-to-charge ratio of a precursor ion and the mass-to-charge ratio of a product ion, as well as a first reference value concerning a measured intensity of the first MRM transition and a second reference value concerning the ratio between the measured intensity of the first MRM transition and a measured intensity of the second MRM transition;

measuring, for each of the target substances, a first intensity which is the measured intensity of the first MRM transition and a second intensity which is the measured intensity of the second MRM transition, by performing an MRM measurement of an analyte sample using the first MRM transition and the second MRM transition set for each of the target substances;

performing, for each of the target substances, a first determination in which the value of the first intensity is compared with the first reference value to determine whether or not the target substance concerned is possibly contained in the analyte sample; and performing, for a target substance considered to be possibly contained in the analyte sample in the first determination, a second determination in which the ratio between the value of the first intensity and the value of the second intensity is compared with the second reference value to determine whether or not the target substance concerned is contained in the analyte sample.

(Clause 3)

A method for analyzing amino acids and/or acylcarnitines according to the second mode of the present invention includes:

setting, for each of one or more target substances each of which is an amino acid or an acylcarnitine, a first MRM transition which is a combination of the mass-to-charge ratio of a precursor ion and the mass-to-charge ratio of a product ion, a reference value concerning a measured intensity of the first MRM transition, as well as a second MRM transition with which a foreign substance that is detectable along with the target substance in an MRM measurement using the first MRM transition is undetectable;

measuring, for each of the target substances, a first intensity which is the measured intensity of the first MRM transition and a second intensity which is the measured intensity of the second MRM transition, by performing an MRM measurement of an analyte sample using the first MRM transition and the second MRM transition set for each of the target substances;

performing, for each of the target substances, a first determination in which the value of the first intensity is compared with the reference value to determine whether or not the target substance concerned is possibly contained in the analyte sample; and performing, for a target substance considered to be possibly contained in the analyte sample in the first determination, a second determination in which whether or not the target substance is contained in the analyte sample is determined based on the value of the second intensity.

In the methods for analyzing amino acids and/or acylcarnitines according to Clauses 1 and 3, a first MRM transition, a second MRM transition, and a reference value (or a first reference value in Clause 1) concerning a measured intensity of the first MRM transition are set for each of one or more target substances each of which is an amino acid or acylcarnitine. An MRM measurement of an analyte sample is performed using the first and second MRM transitions for each target substance. The first MRM transition may be set so that it enables a highly sensitive measurement of the target substance, like the MRM transition used in the conventional mass-screening. The reference value (the same as above) concerning a measured intensity of the first MRM transition may also be set so that it corresponds to the cutoff value used in the conventional mass-screening.

In the methods for analyzing amino acids and/or acylcarnitines according to Clauses 1 and 3, initially, for each target substance, a measured intensity obtained with the first MRM transition is compared with a reference value to determine the possibility that the target substance is contained in the analyte sample (first determination). Conventional mass-screening simply relies on this determination when determining the possibility that the target substance is contained in the analyte sample. Therefore, it has been impossible to discriminate between the case where the target substance is actually contained in the analyte sample and the case where the target substance is not contained and what is actually present is only an isomer or similar foreign substance that can be detected along with the target substance when the first MRM transition is used.

In the method for analyzing amino acids and/or acylcarnitines according to Clause 1, a second reference value is set which concerns the ratio between a measured intensity of the first MRM transition and a measured intensity of the second MRM transition. For a target substance which has been considered to be possibly contained in the analyte sample (first determination), the ratio between the first intensity value and the second intensity value is additionally compared with the second reference value to determine whether or not the target substance is contained in the analyte sample (second determination). Even when a foreign substance that can be detected along with the target substance when the first MRM transition is used is present, there is normally a certain difference between the target substance and the foreign substance in terms of the value of the ratio between the intensity measured by the first MRM transition and the intensity measured by the second MRM transition. In the method for analyzing amino acids and/or acylcarnitines according to Clause 1, when the first determination indicates that the target substance is possibly contained, the aforementioned ratio is compared with the second reference value to determine whether or not the substance contained in the analyte sample is the target substance or a foreign substance (second determination). Therefore, whether or not the target substance is contained in the analyte sample can be determined more accurately than ever before.

In the method for analyzing amino acids and/or acylcarnitines according to Clause 3, a second MRM transition is set which is an MRM transition with which the foreign substance that is detectable along with the target substance concerned in the MRM measurement using the first MRM transition is undetectable. For each target substance considered to be possibly contained in the analyte sample in the first determination, whether or not the target substance concerned is contained in the analyte sample is determined based on the value of a measured intensity (second intensity value) obtained by the second MRM transition (second determination). In the method for analyzing amino acids and/or acylcarnitines according to Clause 3, the determination that the target substance is contained in the analyte sample (second determination) is made based on the condition where the target substance is detected in the MRM measurement using the second MRM transition with which the foreign substance is undetectable. Therefore, whether or not the target substance is contained in the analyte sample can be determined more accurately than ever before.

(Clause 2)

In the method for analyzing amino acids and/or acylcarnitines according to Clause 2, which is one mode of the method for analyzing amino acids and/or acylcarnitines according to Clause 1, the second determination includes:

calculating a score for each of the target substances by using the following equation:

$$\text{Score}=100-(|(\text{Value of measured-intensity ratio of actual sample})-(\text{Reference value of measured-intensity ratio})|/(\text{Reference value of measured-intensity ratio})\times 100)$$, and determining whether or not the target substance concerned is contained in the analyte sample by comparing the value of the calculated score with the second reference value.

In the method for analyzing amino acids and/or acylcarnitines according to Clause 2, the second determination can be performed using a common criterion for all target substances.

(Clause 4)

In the method for analyzing amino acids and/or acylcarnitines according to Clause 4, which is one mode of the method for analyzing amino acids and/or acylcarnitines according to one of Clauses 1-3, the MRM measurement is performed after substances contained in the analyte sample are separated from each other by using a chromatography column.

In the method for analyzing amino acids and acylcarnitines according to Clause 4, since the substances contained in the analyte sample are separated from each other before the MRM measurement, it is possible to more accurately determine whether or not the target substance is contained in the sample.

(Clause 5)

In the method for analyzing amino acids and/or acylcarnitines according to Clause 5, which is one mode of the method for analyzing amino acids and/or acylcarnitines according to one of Clauses 1-3, each of the target substances is either an amino acid selected from the group consisting of phenylalanine, leucine, isoleucine, methionine, citrulline and tyrosine, or an acylcarnitine selected from the group consisting of free carnitine (C0), acetylcarnitine (C2), propionylcarnitine (C3), butyrylcarnitine-palmitoylcarnitine (C4-C18), isovalerylcarnitine, 2-methylbutyrylcarnitine, pivaloylcarnitine (C5), tiglylcarnitine (C5:1), glutarylcarnitine (C5-DC), 3-hydroxyisovalerylcarnitine, 3-hydroxy-2-methylbutyrylcarnitine (C5-OH), octanoylcarnitine (C8), decanoylcarnitine (C10), dodecanoylcarnitine (C12), tetradecenoylcarnitine (C14:1), tetradecanoylcarnitine (C14), palmitoylcarnitine (C16), stearylcarnitine (C18), octadecenoylcarnitine (C18:1), hydroxyhexadecanoylcarnitine (C16-OH) and hydroxyoctadecenoylcarnitine (C18:1-OH).

Each of the target substances in the method for analyzing amino acids and/or acylcarnitines according to Clause 5 is either an amino acid or acylcarnitine associated with a disease of newborns. Therefore, those substances can be suitably used for newborn mass-screening tests.

REFERENCE SIGNS LIST

- 1 . . . Liquid Chromatograph
- 11 . . . Mobile Phase Container
- 12 . . . Pump
- 13 . . . Injector
- 14 . . . Autosampler
- 2 . . . Mass Analyzer
- 20 . . . Ionization Chamber
- 201 . . . Electrospray Ionization (ESI) Probe

21 . . . First Intermediate Vacuum Chamber
211 . . . Ion Lens
212 . . . Skimmer
22 . . . Second Intermediate Vacuum Chamber
221 . . . Ion Guide
23 . . . Analysis Chamber
231 . . . Front Quadrupole Mass Filter
232 . . . Collision Cell
233 . . . Ion Guide
234 . . . Rear Quadrupole Mass Filter
235 . . . Ion Detector
4 . . . Control-and-Processing Unit
41 . . . Storage Section
411 . . . Compound Database (DB)
42 . . . Analysis Condition Setter
43 . . . Measurement Controller
44 . . . First Data Analyzer
441 . . . First Determiner
442 . . . Second Determiner
45 . . . Second Data Analyzer
451 . . . First Determiner
452 . . . Second Determiner
46 . . . Analysis Result Outputter
5 . . . Input Unit
6 . . . Display Unit
C . . . Ion Beam Axis

The invention claimed is:

1. A method for analyzing amino acids and/or acylcarnitines, comprising:

setting, for each of one or more target substances each of which is an amino acid or an acylcarnitine, a first MRM transition and a second MRM transition each of which is a combination of a mass-to-charge ratio of a precursor ion and a mass-to-charge ratio of a product ion, as well as a first reference value concerning a measured intensity of the first MRM transition and a second reference value concerning a ratio between the measured intensity of the first MRM transition and a measured intensity of the second MRM transition;

measuring, for each of the target substances, a first intensity which is the measured intensity of the first MRM transition and a second intensity which is the measured intensity of the second MRM transition, by performing an MRM measurement of an analyte sample using the first MRM transition and the second MRM transition set for each of the target substances;

performing, for each of the target substances, a first determination in which a value of the first intensity is compared with the first reference value to determine whether or not the target substance concerned is possibly contained in the analyte sample; and performing, for a target substance considered to be possibly contained in the analyte sample in the first determination, a second determination in which the ratio between the value of the first intensity and a value of the second intensity is compared with the second reference value to determine whether or not the target substance concerned is contained in the analyte sample.

2. The method for analyzing amino acids and/or acylcarnitines according to claim 1, wherein the second determination includes:

calculating a score for each of the target substances by using a following equation:

Score=100−(|(Value of measured-intensity ratio of actual sample)−(Reference value of measured-intensity ratio)|/(Reference value of measured-intensity ratio)×100), and determining whether or not the target substance concerned is contained in the analyte sample by comparing a value of the calculated score with the second reference value.

3. The method for analyzing amino acids and/or acylcarnitines according to claim 1, wherein the MRM measurement is performed after substances contained in the analyte sample are separated from each other by using a chromatography column.

4. The method for analyzing amino acids and/or acylcarnitines according to claim 1, wherein each of the target substances is either an amino acid selected from the group consisting of phenylalanine, leucine, isoleucine, methionine, citrulline and tyrosine, or an acylcarnitine selected from the group consisting of free carnitine (C0), acetylcarnitine (C2), propionylcarnitine (C3), butyrylcarnitine-palmitoylcarnitine (C4-C18), isovalerylcarnitine, 2-methylbutyrylcarnitine, pivaloylcarnitine (C5), tiglylcarnitine (C5:1), glutarylcarnitine (C5-DC), 3-hydroxyisovalerylcarnitine, 3-hydroxy-2-methylbutyrylcarnitine (C5-OH), octanoylcarnitine (C8), decanoylcarnitine (C10), dodecanoylcarnitine (C12), tetradecenoylcarnitine (C14:1), tetradecanoylcarnitine (C14), palmitoylcarnitine (C16), stearylcarnitine (C18), octadecenoylcarnitine (C18:1), hydroxyhexadecanoylcarnitine (C16-OH) and hydroxyoctadecenoylcarnitine (C18:1-OH).

5. A method for analyzing amino acids and/or acylcarnitines, comprising:

setting, for each of one or more target substances each of which is an amino acid or an acylcarnitine, a first MRM transition which is a combination of a mass-to-charge ratio of a precursor ion and a mass-to-charge ratio of a product ion, a reference value concerning a measured intensity of the first MRM transition, as well as a second MRM transition with which a foreign substance that is detectable along with the target substance in an MRM measurement using the first MRM transition is undetectable;

measuring, for each of the target substances, a first intensity which is the measured intensity of the first MRM transition and a second intensity which is a measured intensity of the second MRM transition, by performing an MRM measurement of an analyte sample using the first MRM transition and the second MRM transition set for each of the target substances;

performing, for each of the target substances, a first determination in which a value of the first intensity is compared with the reference value to determine whether or not the target substance concerned is possibly contained in the analyte sample; and performing, for a target substance considered to be possibly contained in the analyte sample in the first determination, a second determination in which whether or not the target substance is contained in the analyte sample is determined based on a value of the second intensity.

6. The method for analyzing amino acids and/or acylcarnitines according to claim 5, wherein the MRM measurement is performed after substances contained in the analyte sample are separated from each other by using a chromatography column.

7. The method for analyzing amino acids and/or acylcarnitines according to claim 5, wherein each of the target substances is either an amino acid selected from the group consisting of phenylalanine, leucine, isoleucine, methionine, citrulline and tyrosine, or an acylcarnitine selected from the group consisting of free carnitine (C0), acetylcarnitine (C2), propionylcarnitine (C3), butyrylcarnitine-palmitoylcarnitine (C4-C18), isovalerylcarnitine, 2-methylbutyrylcarnitine, pivaloylcarnitine (C5), tiglylcarnitine (C5:1), glutarylcarnitine (C5-DC), 3-hydroxyisovalerylcarnitine, 3-hydroxy-2-methylbutyrylcarnitine (C5-OH), octanoylcarnitine (C8), decanoylcarnitine (C10), dodecanoylcarnitine (C12), tetradecenoylcarnitine (C14:1), tetradecanoylcarnitine (C14), palmitoylcarnitine (C16), stearylcarnitine (C18), octadecenoylcarnitine (C18:1), hydroxyhexadecanoylcarnitine (C16-OH) and hydroxyoctadecenoylcarnitine (C18:1-OH).

* * * * *